United States Patent [19]
Wacker et al.

[11] Patent Number: 4,971,523
[45] Date of Patent: Nov. 20, 1990

[54] DUAL DIAPHRAGM APPARATUS WITH DIAPHRAGM ASSEMBLY AND RUPTURE DETECTION METHODS

[75] Inventors: Robert L. Wacker, Wellington; James Kennon, Amherst; Kevin C. Becker, Westlake; Harry J. Lader, Lakewood; William R. Rehman, Vermilion, all of Ohio

[73] Assignee: Nordson Corporation, Westlake, Ohio

[21] Appl. No.: 243,802

[22] Filed: Sep. 13, 1988

[51] Int. Cl.$^5$ .................. F04B 39/04; F04B 43/04
[52] U.S. Cl. .................... 417/63; 417/413; 417/271; 340/605; 92/5 R; 92/98 R
[58] Field of Search .......... 417/63, 420, 413, 269, 417/271; 340/604, 605; 92/5 R, 98 R, 103 R, 103 SD

[56] References Cited

U.S. PATENT DOCUMENTS

| | | |
|---|---|---|
| 2,323,950 | 7/1943 | Wade . |
| 2,645,248 | 7/1953 | Baker . |
| 2,662,478 | 12/1953 | Surre ........................... 417/63 |
| 3,131,638 | 5/1964 | Wilson et al. . |
| 3,361,077 | 1/1968 | Freeman ........................ 417/269 |
| 3,431,823 | 3/1969 | Orlita . |
| 3,605,566 | 9/1971 | Vetter . |
| 3,661,060 | 5/1972 | Bowen ........................ 417/63 X |
| 3,775,030 | 11/1973 | Wanner . |
| 3,884,598 | 5/1975 | Wanner . |
| 4,569,634 | 2/1986 | Mantell ......................... 417/63 |
| 4,781,535 | 11/1988 | Frawley et al. ................ 92/5 R X |
| 4,838,763 | 6/1989 | Kramer et al. ............... 417/420 X |

FOREIGN PATENT DOCUMENTS

| | | |
|---|---|---|
| 1403804 | 12/1968 | Fed. Rep. of Germany . |
| 1453454 | 2/1969 | Fed. Rep. of Germany ...... 417/395 |
| 2624129 | 3/1977 | Fed. Rep. of Germany . |
| 63-11196 | 5/1988 | Japan . |

*Primary Examiner*—Leonard E. Smith
*Assistant Examiner*—Eugene L. Szczecina, Jr.
*Attorney, Agent, or Firm*—Wood, Herron & Evans

[57] ABSTRACT

A diaphragm assembly includes a pair of superposed flexible diaphragms adhesively secured to an annular spacer ring. The space between the diaphragms and the interior of the rings is filled preferably with de-ionized water. The resistivity of the water is monitored to detect conductivity changes upon leakage or diaphragm rupture when pumped materials or pump lubricant mix with the water. Diaphragm assembly and rupture detection methods are disclosed.

18 Claims, 1 Drawing Sheet

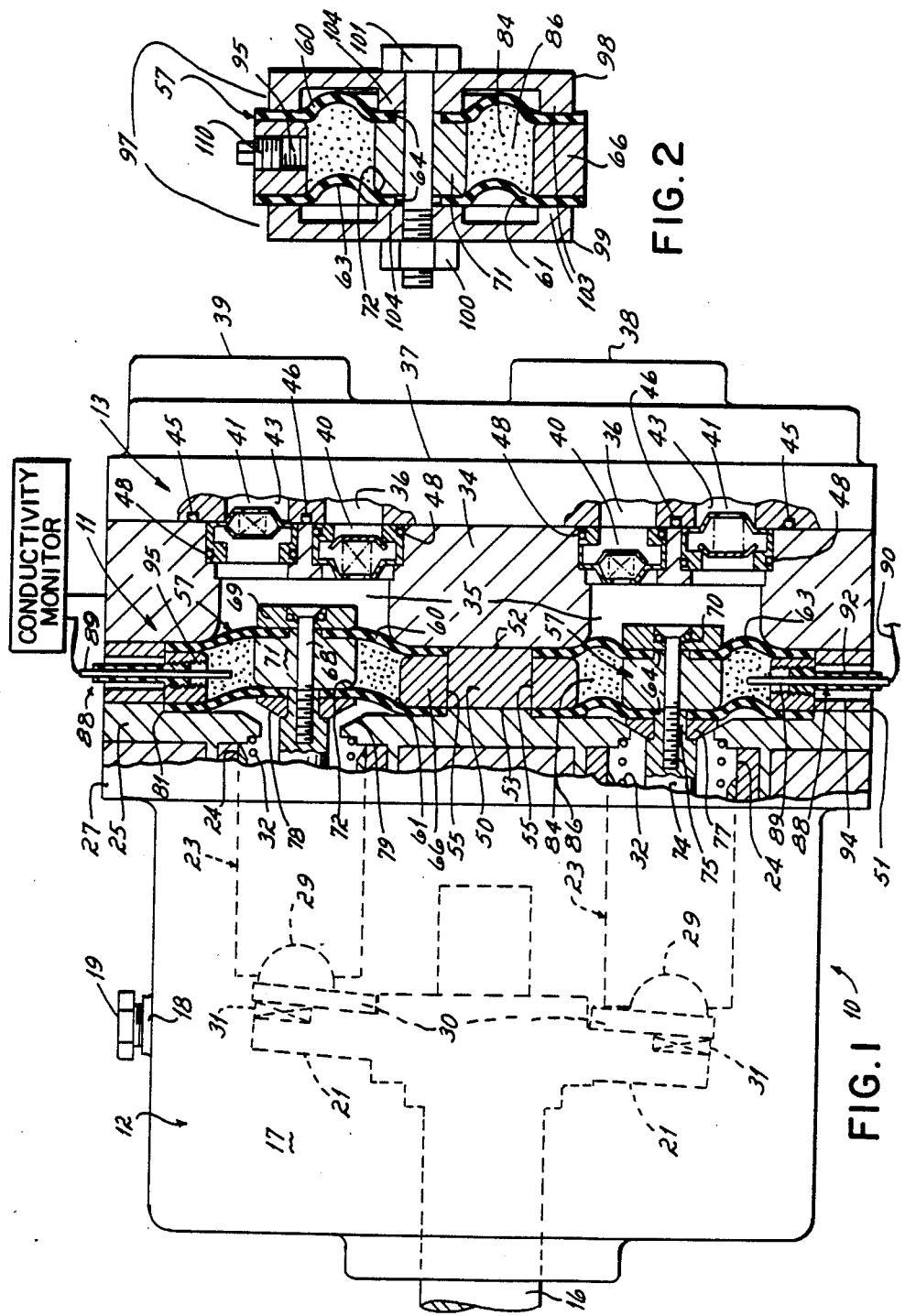

DUAL DIAPHRAGM APPARATUS WITH DIAPHRAGM ASSEMBLY AND RUPTURE DETECTION METHODS

FIELD OF THE INVENTION

The present invention relates to diaphragm pumps and, more particularly, to a dual diaphragm apparatus interposed between a drive assembly and a valve assembly of a pump to maintain isolation of the fluid being pumped from the drive assembly lubricant.

BACKGROUND OF THE INVENTION

In many fluid handling applications such as, for example, the pumping of coating material in a system for coating the interior of can bodies, it is important to maintain isolation of the material or delivery medium being pumped from the lubricant used in the pumping apparatus. Contamination of the lubricant by the pumped material may cause damage to the pump. Moreover, mixing of lubricant from the pump with the pumped material can impair the properties of the pumped material. Thus in a can coating system, contamination of the coating material by the lubricant may render the coating material toxic or otherwise impair proper functioning of the coating.

In the past, a diaphragm type pump has been used to avoid mixing of any lubricant with a delivery medium being pumped. In such diaphragm pumps, one or more flexible diaphragms serve as fluid barriers as well as mechanical couplings between a lubricated drive assembly and a pumping chamber. Typically, the drive assembly supplies a motive force which is transferred through the diaphragm to the delivery medium contained in a pumping chamber. The pumping chamber includes an inlet, an outlet and respective associated valve assemblies for controlling the flow of the pumped fluid to and from the pumping chamber.

One example of such a diaphragm pump is illustrated in Wanner U.S. Pat. No. 3,775,030, the disclosure of which is expressly incorporated herein by reference in its entirety to form part of this application. The Wanner patent discloses a diaphragm pump having three identical sets of single diaphragms disposed at 120 degree intervals for sequential actuation by respective associated piston assemblies, each of which is reciprocably driven by a rotatably driven cam plate. The pistons and cam plate form part of the drive assembly which is bathed in hydraulic pumping and lubricating fluid. As the pistons reciprocate, they flex the diaphragms to pump fluid material in the pumping chamber from an inlet to an outlet through respective valve assemblies. The hydraulic lubricating or pumping fluid is separated from the fluid material being pumped in the pumping chamber by only the single diaphragms. Thus, if any of the three diaphragms should rupture, undesired mixing of hydraulic fluid with the material being pumped would occur. Since the pump includes no means to detect such mixing, that adverse condition would be likely to persist for some period of time, perhaps worsening, before being detected so that appropriate corrective action could be initiated.

One possible solution to these problems is proposed in U.S. Pat. No. 3,131,638 wherein each diaphragm device comprises three or more diaphragms arranged in superposed layers. Failure of a single diaphragm will not result in mixing of lubricant and the delivery medium. Moreover, any rupture and leakage through one of the outer two diaphragms is monitored. Particularly, one of the center diaphragms is perforated with radial slots communicating with the environment. Leaking material is transmitted outwardly therethrough into a leak indicating device. This allows monitoring any leakage of hydraulic fluid or the delivery medium being pumped to indicate failure of one of the outer diaphragms.

In another diaphragm pump assembly, as shown in U.S. Pat. No. 3,605,566, the space between dual diaphragms is filled with a hydraulic medium supplied from a tank. If a diaphragm ruptures, either hydraulic fluid or delivery medium flows into the tank where its presence can be sensed by means of noting the increased tank volume.

Because the contaminating fluid in each of these devices must make its way into a tank some distance from the leak and because the sensible concentration of the contaminant is diluted by the volume of hydraulic medium in the tank, sensing a rupture may be unduly delayed. Also, the tank and necessary piping connections are bulky and cumbersome to assemble and maintain.

Another device to monitor rupture of one of two diaphragms, and resultant fluid leakage, is disclosed in U.S. Pat. No. 3,431,823. The space between a pair of diaphragms is filled with a buffer fluid which hydraulically couples the two diaphragms together, eliminating one lifting off from the other. If the buffer fluid is contaminated by either pumped material or pumping fluids, its pH is changed. This change is sensed by an electrode disposed in the fluid filled region between the diaphragms.

Despite these attempts, problems still exist in dual diaphragm pumps. Detection of leakage can be delayed. Moreover, the sensing of a pH change may require an increased concentration of contaminant in the buffer fluid before a leak signal can be generated. This could permit, in the case of rupture of the diaphragm on the pumped material side, at least leakage of the buffer material into the pumped fluid without detection for some time.

In another aspect of such pumps, the assembly of the dual diaphragms is complicated. Such a combined diaphragm device might typically include both diaphragms, intermediate spacers, and the "buffer" fluid. It is difficult to hold these parts together during assembly without losing the buffer fluid.

One attempted solution to this difficulty is discussed in U.S. Pat. No. 3,431,823. The diaphragm assembly comprises a structural unit wherein each diaphragm is initially clamped between an inner support and one of a pair of clamping rings so that the unit may be filled with buffer fluid prior to assembly. Once the unit is assembled into a pump, the pump casing clamps the diaphragms at a point radially inwardly of the point held by the clamping rings. Thus, the clamping rings do not get in the way of the pump casing faces. After assembly, the clamping rings serve no significant purpose.

Accordingly, it has been one objective of the invention to provide an improved, sensitive, quick-acting leak or diaphragm rupture detection apparatus.

It has been a further objective of the invention to provide an improved dual diaphragm apparatus facilitating diaphragm to pump assembly, and the scheduled or emergency replacement of the diaphragm apparatus without loss of buffer fluid.

SUMMARY OF THE INVENTION

To these ends, a preferred embodiment of the invention includes a pair of opposed diaphragms separated by an annular ring wherein the gap between the diaphragms interiorly of the ring is prefilled with distilled, de-ionized water as a buffer fluid. An electrode is inserted through a space between the diaphragms to sense changes in the conductivity capacity of the water. Minute leaks of lubricant or pumped fluids into the buffer fluid are readily and quickly detectable by such sensing. The improved diaphragm apparatus includes an annular ring with opposed circumferential selvage areas of each diaphragm adhesively joined to outward faces of the ring. A split housing is clamped over the diaphragm/ring assembly to maintain the diaphragms in register with the ring during storage or shipment of the assembly.

A radial bore is disposed in the ring and provides a passage through which the de-ionized buffer fluid is introduced. Thereafter, air is purged and an insulated sensor electrode is disposed in the bore, extending into the buffer fluid between the diaphragms.

When the diaphragm assembly is to be installed, the split housing is removed and the adhesive holds the diaphragms to the ring until the assembly is clamped in the pump. No buffer fluid is lost.

The improved diaphragm assembly also includes a plate provided with apertures adapted to receive diaphragm assemblies at appropriate driving locations of the pump for those pumps having multiple sequentially actuated diaphragm assemblies. Radial bores extending between the plate edges and the plate apertures align with the bores in the diaphragm rings for receiving the electrode sensors. This plate helps to align and properly register the diaphragm assemblies and, as will be described, facilitates handling of the leak or rupture sensors. The combination of the plate and diaphragm assemblies thus constitutes a diaphragm module providing the various advantages described herein.

BRIEF DESCRIPTION OF THE DRAWINGS

FIG. 1 is a side view of a diaphragm pump partially in cross-section and partially in elevation, illustrating a preferred embodiment of a diaphragm assembly constructed in accordance with the invention.

FIG. 2 is a cross-sectional view of a housing for storage and shipping of a portion of the diaphragm assembly of the invention.

DETAILED DESCRIPTION OF THE INVENTION

Referring now to FIG. 1, there is shown a diaphragm pump 10 incorporating a preferred embodiment of an improved diaphragm assembly indicated generally at 11 constructed according to the present invention. Except for diaphragm assembly 11, pump 10 is otherwise of a conventional type such as a model D10-S manufactured by Wanner Engineering, Inc. of Minneapolis, Minn. whose construction and operation is more fully described in U.S. Pat. No. 3,775,030 previously incorporated by reference herein.

Pump 10 consists generally of a diaphragm assembly 11, interposed between a drive assembly 12 for actuating the diaphragm assembly 11 and a valve assembly 13 for controlling the flow of a delivery medium being pumped.

Drive assembly 12 includes a shaft 16 coupled to an electric motor (not shown) for supplying a motive force. Shaft 16 is journalled for rotation within a pump housing 17 the interior of which is bathed in a suitable lubricant which may be filled through an inlet 18 in housing 17 pluggable with breather cap 19. Shaft 16 carries a circular cam plate 21. Rotary motion thereof is converted to a reciprocating action of three sets of piston assemblies 23 which travel in respective cylinders 24 projecting inwardly of housing 17. Cylinders 24 are formed integrally with a cylinder plate 25 which is secured to an outwardly projecting flange 27 formed at the forward end of housing 17. The base of piston assembly 23 is fitted with a hemispherical foot 29 retained by a ring 30 which in turn is supported by a bearing 31 interposed between ring 30 and cam plate 21. Cam plate 21 is canted with respect to shaft 16 so that as cam plate 21 rotates, piston assemblies 23 reciprocate by virtue of their indirect engagement with the surface of cam plate 21. Thus, piston assemblies 23 are sequentially actuated by cam plate 21. The return stroke of piston assemblies 23 is facilitated by return springs 32 lying between each piston assembly 23 and cylinder plate 25.

Valve assembly 13 includes a valve plate 34 which defines three cylindrical pumping chambers 35, each of which is axially aligned with one of the piston assemblies 23 of drive assembly 12. Also included in valve assembly 13 is a manifold plate 37 which includes an inlet 38 and an outlet 39 for the delivery medium or pumped fluid, each provided with suitable internal threads (not shown) to facilitate piping connections thereto.

Inlet 38 communicates with each pumping chamber 35 by way of inlet passages 36 formed in manifold plate 37, through a corresponding suction valve 40 to permit delivery medium to enter pumping chamber 35. Similarly, each pumping chamber 35 communicates with a corresponding discharge valve 41 each of which is aligned with an outlet passage 43 formed as a single annular groove in the face of manifold plate 37 and connected to outlet 39 for discharging delivery medium. Passages 36 and 43 are sealed by an outer O-ring 45 and an inner O-ring 46, each of which is seated in the face of manifold plate 37. Valves 40 and 41 are each seated in the opposing face of valve plate 34 and sealed in their seats by means of O-rings 48. Manifold plate 37, valve plate 34, diaphragm assembly 11 and cylinder plate 25 are secured together and to pump housing 17 in the positions shown by means of suitable bolts (not shown).

Diaphragm assembly 11 lies between cylinder plate 25 and valve assembly 13. The diaphragm assembly or module 11 preferably includes a circular diaphragm plate 50 having a bounding edge surface 51, a front face 52 mateable with the valve plate 34 of valve assembly 13 and an opposed rear face 53 mateable with the cylinder plate 25 of drive assembly 12. Diaphragm plate 50 includes three identical apertures 55 spaced at 120 degree intervals to align axially with one of the piston assemblies 23 and its corresponding pumping chamber 35. Each aperture 55 is sized to receive a respective diaphragm subassembly 57 in a fit having a slight clearance.

It should be noted that while three each of piston assemblies 23, diaphragm subassemblies 57, pumping chambers 35 and sets of valves 40, 41 have been described, the section view of FIG. 1 is taken through the centers of two sets of these components at a 120 degree angle so that the third set is not visible, this view being sufficient for a complete understanding of the invention. The set of these components shown at the top of FIG. 1 are shown in their positions at full forward or discharge stroke while the set at the bottom portion of FIG. 1 are shown in their positions at full rearward or intake stroke.

Each diaphragm subassembly 57 includes a front diaphragm 60 and a superposed rear diaphragm 61 each made of flexible material selected to be impenetrable by and reasonably resistant to degradation by both the lubricant bathing the interior of drive assembly 12 and the delivery medium. BUNA-N rubber is suitable for use as a diaphragm material with the commonly used can coating materials with which applicant is acquainted and with S.A.E. 30 detergent type motor oil as a pump lubricant. As is visible in the lower portion of FIG. 1, which shows diaphragms 60 and 61 substantially in their relaxed state, each diaphragm 60, 61 includes a forwardly directed annular convolution 63. Each diaphragm 60, 61 also includes a central hole 64, the perimeter of which preferably includes a forwardly directed raised lip (not shown) for reinforcement and sealing. The perimeter of each diaphragm 60, 61 also preferably includes a forwardly directed raised solid lip (not shown) for sealing.

Diaphragms 60 and 61 are spaced apart at their peripheries by an annular diaphragm ring 66 which preferably includes radiused inner and outer edges on both sides thereof. Diaphragms 60 and 61 are secured to one another and ultimately to one of piston assemblies 23 by means of a flat head slotted screw 68, the head of which is recessed in a follower member 69 and sealed with respect thereto by means of an O-ring 70. Screw 68 passes through the center of a spacer member 71 disposed between diaphragms 60 and 61 and having a radiused edge 72. Screw 68 threadably engages the forward end 74 of piston assembly 23 which includes a projecting hub 75 onto which is press fitted a plunger 77. Plunger 77 includes a chambered face 78 which is mateable with a corresponding tapered seat 79 formed in cylinder plate 25. Cylinder plate 25 also includes a recessed seat 81 for each rear diaphragm 61. When pump 10 is assembled, the perimeter portion of each diaphragm 60 and 61 is clamped between ring 66 and valve plate 34 and cylinder plate 25 respectively with sufficient pressure to form effective fluid seals.

The invention contemplates filling the annular gap 84 defined by the opposed inner surfaces of diaphragms 60 and 61, the interior surface of ring 66 and the cylindrical surface of spacer 71 with a buffer fluid medium 86 preferably comprising distilled, de-ionized, water. Buffer fluid or medium 86 should be substantially free of voids or bubbles of air or other gases so that diaphragms 60 and 61 are hydraulically, as well as mechanically coupled to insure they move with one another in unison. To facilitate detection of a rupture of diaphragms 60 or 61, medium 86 a predetermined electrical resistance which undergoes a change which can be quickly detected upon contamination of medium 86 by amounts of lubricant, delivery medium or both. In applications where the delivery medium is a food or a material likely to contact food, such as the coating material used to coat the interior of can bodies, it is also important that medium 86 be hypotoxic.

To detect a rupture of either diaphragms 60 or 61, diaphragm assembly 11 preferably includes means for sensing contamination of medium 86 by lubricant, delivery medium or both. While many different sensors can suitably be used for this purpose, applicant prefers to use a conductivity probe 88. Probe 88 comprises a metallic electrode 89 connected to a lead wire 90 and press fitted in an externally threaded bushing 92 of plastic or other electrically insulating material.

Plate 50 is provided with bores 94 extending between bounding edge surface 51 and apertures 55. The bores 94 have sufficient clearance for bushings 92 and are aligned with respective threaded radial bores 95 traversing annular rings 66. Bushings 92 threadably engage bores 95 so that electrodes 89 protrude into the respective gaps 84 in intimate contact with medium 86. Conductivity monitoring means 120, which may include an alarm or other suitable output function generating means is connected between electrode 89 and the pump to monitor any change in the conductivity of the buffer medium between electrode 89 and pump 10. Such changes are indicative of mixing of delivery medium or lubricant with medium 86 whereby an appropriate indication alarm or response may be given, for example, pump 10 may be deenergized or other appropriate corrective action initiated.

In this regard, it will be appreciated that both the lubricating or pumping fluid, and the pumped fluid or material are generally more conductive than the de-ionized buffer fluid between the diaphragms. It is also preferred that both lubricating fluid and the pumped materials be water soluble.

Accordingly, with the initial conductivity of the de-ionized water predetermined, the conductivity monitor means 120 may be preset to sense or respond to a rise in the conductivity (or decrease in resistivity) of the buffer fluid as would indicate contamination of the fluid with a contaminant of higher conductivity, Also, the target conductivity at which the conductivity monitor will indicate a leak should be high enough so that any inherent change in the resistivity of the buffer medium due, for example, to ion leaching from the diaphragms will not cause generation of a response by monitor 120.

It is, of course, desirable to provide an indication of rupture or of leakage at the earliest possible time. In this regard, the conductivity or resistivity set point of the monitor 120 is set as closely as possible to that of de-ionized water. Such a close setting will provide a contaminant or leakage alarm for even extremely small leaks or ruptures, indicating need for pump stoppage and diaphragm replacement. It is contemplated that the diaphragm assemblies will be replaced before any inherent conductivity change in the buffer would cause the monitor 120 to activate a response.

For example, we have found the Buna-N diaphragm mentioned earlier slowly leaches ions causing the de-ionized water to become more conductive with time, under ambient and static conditions and after the diaphragm had been washed a number of times. Thus a resistivity level measured through the diaphragm buffer fluid of de-ionized water might be 10,000 ohm-cm at about 0.7 years and may decrease to 8,000 ohm-cm at 1.1 years, 5,000 ohm-cm at 3 years and 1,000 ohm-cm at 110 years.

In order that the leaching of ions from the diaphragm does not trigger the predetermined resistivity or alarm set point prematurely, a set point lower than the lowest resistivity value over a given period of time must be assigned. Therefore, if the diaphragms were to be changed routinely once a year, for example, a set point of 8,000 ohm-cm can be assigned without any fear that the leaching of ions from the diaphragm will set off the alarm over the 1 year period. At the same time, any materials used in the assembly of the diaphragm assembly must be chosen to minimize contamination of the de-ionized water to prevent premature alarm. Alternatively, a diaphragm material which does not leach ions could be used.

In order to arrive at a set-point resistivity below which an alarm is triggered, the resistivity of the material on either side of the de-ionized water needs to be evaluated.

For example, in a can-coating process, a coating material provided by the Glidden Corporation under its designation 640-C-552 can be used and constitutes the pumped material. A predetermined set point of 8,000 ohm-cm is reached at only about 2% dilution of buffer fluid by this material. This result means that as little as 2% of the can coating mixing with the de-ionized water is sufficient to trigger an alarm to alert the operator that the diaphragm has ruptured.

On the other side, the normally expected conductivity of the formulated lubricant, such as an S.A.E. 30 petroleum-based oil means that a dilution of 12% of the buffer fluid must be reached before the 8,000 ohm-cm set point is attained. That is, a greater degree of rupture with more mixing must occur before an alarm alerting the operator has occurred. This increased degree of diaphragm rupture on this side is not a problem as long as rupture between the de-ionized water and the coating has not occurred which could contaminate the coating. Furthermore, the lubricant can be formulated to be more conducting by the addition of salts such as sodium nitrite so that the set point resistivity will be achieved at a lower dilution.

It will be thus appreciated that the conductivity set point at which a rupture or leak response is generated will vary according to a number of factors including actual diaphragm materials and preparation (i.e. washing, treating, etc.) buffer fluid selection, pumped material, lubricating material, scheduled diaphragm replacement frequencies and the like, all of which can be determined and pre-selected according to the invention.

In another aspect of the present invention, the method whereby diaphragm assembly 11 is assembled and affixed to pump 10 will now be described.

Diaphragm subassembly 57 is assembled by centering diaphragm ring 66 and spacer 71 atop rear diaphragm 61. Diaphragm 60 is disposed in register with ring 66, diaphragm 61 and spacer 71 and the diaphragms are adhered to the ring about their salvage area with any appropriate adhesive.

As shown in FIG. 2, the assembly of the two diaphragms, spacer and ring are clamped within a split housing 97 having a front half 98 and a rear half 99 secured by a nut 100 and bolt 101. Each half 98 and 99 includes an outer land 103 and an inner land 104 which respectively clamp portions of diaphragms 60 and 61 against ring 66 and spacer 71. Thus, housing 97 serves to maintain the proper alignment of diaphragms 60, 61, ring 66 and spacer 71 and prevent the migration of air bubbles into buffer fluid 86 during storage or shipping of diaphragm subassembly 57. After such clamping, the gap 84 between the diaphragms is filled with the de-ionized water buffer fluid through bore 95. The assembly is then placed in an evacuation chamber to purge air and bore 96 is plugged by plug 110, or by the sensor.

Diaphragm subassembly 57 is mounted to pump 10 in the following manner. With drive assembly 12 completely assembled and valve assembly 13 assembled but not yet installed, shaft 16 is rotated until one of the piston assemblies 23 assumes its top dead center (fully forward) position as shown at the top of FIG. 1. The housing 97 is removed from the diaphragm assembly with the adhesive holding it together and the assembly is disposed such that diaphragm 61 lies in recess 81 in the cylinder plate 25. Screw 68 is then threaded into the forward end 74 of that piston assembly and tightened so that plunger 77 is pressed onto hub 75. Taking care not to jar each installed subassembly, the above procedure is repeated to attach the remaining two diaphragm subassemblies 57. During this procedure, medium 86 does not leak from between diaphragms 60 and 61 due to the adhesive bound assembly. At this point, air may be purged from each piston assembly 25. This is done by rotating shaft 16 a few times until any signs of air escaping from beneath diaphragm 61 disappear.

Assembly continues by placing diaphragm plate 50 so that each subassembly 57 aligns with a respective one of apertures 55. The rear face 53 of plate 50 is fitted flush against the opposing face of cylinder plate 25 so that each diaphragm ring 66 is received within its respective aperture 55. Each diaphragm subassembly 57 may then be loosened slightly by loosening screw 68 and rotated so that the radial bore 95 in ring 66 aligns with a respective one of the bores 94 in plate 50. Screw 68 is then retightened.

Valve assembly 13, which has been previously assembled, is then aligned so that each pumping chamber 35 is axially aligned with one of diaphragm subassemblies 57. The face of valve plate 34 contiguous with pumping chambers 35 mates flush against the front face 52 of diaphragm plate 50. Valve assembly 13, diaphragm assembly 11 and drive assembly 12 are then secured in the position shown in FIG. 1 by means of bolts (not shown).

Probes 88, if not pre-installed so that their portions extending beyond rings 66 are already inserted in bores 94 of plate 50 during diaphragm positioning, are assembled by attaching leadwire 90 to one end of metal electrode 89 by brazing or other suitable means. The other end of electrode 89 is then press fitted through the center of electrically insulating bushing 92 as to protrude slightly from the end thereof. Each probe 88 is then passed through bores 93 with leadwire 90 extending outwardly therefrom for connection with a suitable conductivity monitoring device. Bushing 92 is threaded into ring 66 by way of radial bore 95 so that electrode 89 protrudes into gap 84 and is immersed in medium 86. This, too, can be done under any appropriate air purging environment.

In the alternative, a complete module, including plate 50 and pre-positioned diaphragm subassemblies 57 can be substituted for a used plate and worn diaphragm subassemblies, it only being necessary to remove the original plate and diaphragms, to insert the new assembly module, removing the split portions of housings 97, and attaching the diaphragms by screws 68 to the respective pistons and to assemble the valve assembly 13 to the plate and pump combination, thus greatly facilitating diaphragm replacement.

In normal operation, shaft 16 is rotatably driven to rotate cam plate 21 to sequentially reciprocate piston assemblies 23. The reciprocating motion of the forward end 74 of piston assembly 23 is imparted to diaphragms 60 and 61 such that front diaphragm 60 pumps the delivery medium. On the forward stroke of diaphragms 60 and 61, as illustrated at the top of FIG. 1, suction valve 40 is closed. Delivery medium inside pumping chamber is forced outward through discharge valves 41 to outlet passage 43 and outlet 39. On the return stroke of diaphragms 60 and 61, as illustrated at the bottom portion of FIG. 1, discharge valve 41 is closed and delivery medium is drawn into pumping chamber 35 from inlet 38 by way of inlet passage 36 through suction valve 40. Thus delivery medium is continuously pumped from inlet 38 to outlet 39. Because the electrode 89 is in contact only with medium 86, the conductivity between electrode 89 and another reference point on the metallic structure of pump 10 remains at a normal value to be sensed by conductivity monitoring means (not shown).

In the event that either front diaphragm 60 and/or rear diaphragm 61 should rupture or become dislodged, delivery medium and/or lubricant respectively would mix with medium 86 thereby immediately changing its electrical conductivity. This change would be sensed by electrode 89 and its associated monitoring means to stop pump 10 promptly and/or initiate other appropriate corrective actions or indications.

While the apparatus and methods herein described constitute a preferred embodiment of this invention, it is to be understood that the invention is not limited to this form of apparatus or particular method steps and that changes may be made therein without departing from the scope of the invention. Applicant is thus bound only by the appended claims.

What is claimed is:

1. A diaphragm assembly for a diaphragm pump of the type having a lubricant-bathed drive assembly and a valve assembly having a plate including inlet and outlet valves for controlling the flow of a delivery medium being pumped with a diaphragm assembly operably coupled to said drive assembly to pump said delivery medium while maintaining isolation of said lubricant therefrom, said diaphragm assembly comprising:
    (a) a first diaphragm and a second diaphragm each having opposed inner surfaces;
    (b) an annular ring disposed between said diaphragms separating said inner surfaces thereof to define a gap therebetween,
    (c) a fluid buffer medium disposed within said gap and;
    (d) a diaphragm plate adapted for mounting between the drive assembly and the valve assembly of the pump, said plate having a bounding edge surface, a front face mateable with said valve assembly and an opposed rear face mateable with said drive assembly, said plate including at least one aperture adapted to receive said annular ring.

2. The assembly of claim 1 wherein said fluid buffer medium comprises de-ionized water and wherein said annular ring includes a first bore communicating with said gap, said first bore being adapted to receive a sensor responsive to increased conductivity of said fluid material by the mixing therewith of at least one of said lubricant and said delivery medium.

3. The assembly of claim 2 wherein said plate includes a second bore extending between said bounding edge surface and said aperture, said second bore being in register with said first bore to provide sensor access to said fluid buffer medium, facilitate insertion and removal of said sensor.

4. The assembly of claim 1 wherein said fluid medium has a resistivity of 10,000 ohm-cm during its first 6 months of operation.

5. The assembly of claim 1 wherein said fluid medium has a resistivity of 8,000 ohm-cm during its first year of operation.

6. A diaphragm assembly for a diaphragm pump of the type having a lubricant-bathed drive assembly and a valve assembly for controlling the flow of a delivery medium being pumped with a diaphragm assembly operably coupled to said drive assembly to pump said delivery medium while maintaining isolation of said lubricant therefrom, said diaphragm assembly comprising:
    (a) a first diaphragm and a second diaphragm each having opposed inner surfaces;
    (b) an annular ring disposed between said diaphragms separating said inner surfaces thereof to define a gap therebetween, and
    (c) a fluid buffer medium disposed within said gap; and
    (d) said first and second diaphragms having respective opposed selvage areas adhesively secured to adjacent faces of said ring.

7. A diaphragm module for a diaphragm pump, said module comprising:
    a diaphragm plate having at least one aperture therein;
    a dual diaphragm means disposed in said aperture said dual diaphragm means including first and second diaphragms having opposed inner surfaces and an annular ring disposed between said surfaces and defining a gap therebetween;
    said dual diaphragm means a buffer medium therebetween, and
    said diaphragm module further including at least one sensing means extending through said plate and said ring and into said buffer medium for sensing rupture of at least one of said diaphragms.

8. A diaphragm module as in claim 7 wherein said plate includes at least two apertures, and a dual diaphragm means in each aperture.

9. A diaphragm module as in claim 8 further including a plurality of sensing means in said plate, one extending respectively into the buffer medium of each dual diaphragm.

10. A method of assembling a diaphragm assembly of a diaphragm pump having a drive assembly, and a valve assembly with a diaphragm assembly clamped therebetween when the pump is assembled, said method comprising the steps of:
    adhesively securing opposed selvage areas of two diaphragms to an annular ring interposed therebetween;
    clamping the diaphragms and ring between two clamping members;
    filling spaces between said diaphragms and interiorly of said ring with a fluid buffer medium to form a diaphragm assembly;
    said diaphragms remaining adhered to said ring upon removal of said clamping members for installation of said diaphragm assembly in a diaphragm pump.

11. The method of claim 10 further comprising the step of placing said diaphragm assembly in an evacuated chamber to purge any gas bubbles and voids therefrom.

12. The method of claim 10 further comprising the step of inserting an electrode into said buffer fluid medium for monitoring a change in the conductivity characteristics thereof to detect a failure of one of said diaphragms.

13. A method of replacing a dual diaphragm in a pumping apparatus having a pump drive and a valve apparatus having inlet and outlet valves and comprising the steps of:
- removing used diaphragms from said pump apparatus;
- inserting a plate containing at least one dual diaphragm assembly including two diaphragms and an annular ring disposed therebetween defining a gap between said diaphragms in an aperture in said plate in register between said pump drive and said valve apparatus; and
- clamping said plate and dual diaphragm apparatus therein between said pump drive and said valve apparatus.

14. A method as in claim 13 wherein said diaphragm assembly further includes a buffer medium comprising de-ionized water.

15. A diaphragm pump, comprising:
- a drive assembly which is lubricated by a lubricant material;
- a valve assembly for controlling the flow of a delivery medium and including a valve plate with respective inlet and outlet valves; and
- at least two diaphragm assemblies which are operatively coupled to said drive assembly to pump said delivery medium while maintaining isolation of said lubricant material from said delivery medium to prevent the contamination of said delivery medium by said lubricant material, each of said diaphragm assemblies comprising a first diaphragm and a second diaphragm having opposed inner surfaces, and an annular ring having said diaphragms secured thereto to separate said inner surfaces of said diaphragms from one another to define a gap therebetween, with a fluid medium disposed within said gap; and
- a diaphragm plate adapted for mounting between said drive assembly and said valve assembly, said diaphragm plate having at least two apertures therein, with one of said diaphragm assemblies disposed within each of said apertures.

16. The diaphragm pump of claim 15 wherein each annular ring of each diaphragm assembly includes a passage communicating with said gap, said passage being adapted to receive a means for sensing a change in said fluid medium caused by the mixing of some of said lubricant material or some of said delivery material in which said fluid medium due to leakage or the rupture of one of said diaphragms.

17. The diaphragm pump of claim 16 wherein said sensing means senses a change in the electrical conductivity of said fluid medium.

18. The diaphragm pump of claim 16 wherein said diaphragm plate includes passages which align with said passages in said annular rings, and wherein a portion of each sensing means of each diaphragm assembly extends through one of said passages in said diaphragm plate and through said passage in said annular ring of each diaphragm assembly.

* * * * *